United States Patent
Björk

(12) 
(10) Patent No.: US 6,355,897 B1
(45) Date of Patent: Mar. 12, 2002

(54) ARRANGEMENT AND METHOD FOR SORTING GRANULES

(75) Inventor: Svante Björk, Kungsbacka (SE)

(73) Assignee: Svante Björk AB, Kungsbacka (SE)

( * ) Notice: Subject to any disclaimer, the term of this patent is extended or adjusted under 35 U.S.C. 154(b) by 0 days.

(21) Appl. No.: 09/554,150
(22) PCT Filed: Nov. 24, 1997
(86) PCT No.: PCT/SE97/01971
 § 371 Date: May 9, 2000
 § 102(e) Date: May 9, 2000
(87) PCT Pub. No.: WO99/29442
 PCT Pub. Date: Jun. 17, 1999

(51) Int. Cl.[7] ............................................. B07C 5/342
(52) U.S. Cl. ...................... 209/588; 209/577; 209/382
(58) Field of Search ........................ 356/237.1, 237.2, 356/244; 209/576, 577, 585, 588, 581, 582

(56) References Cited

U.S. PATENT DOCUMENTS

| | | | | |
|---|---|---|---|---|
| 3,515,273 A | * | 6/1970 | Seaborn ....................... 356/318 |
| 3,628,657 A | * | 12/1971 | Billett ......................... 209/579 |
| 3,890,221 A | * | 6/1975 | Muehlethaler .............. 209/577 |
| 3,922,557 A | * | 11/1975 | Carnes Jr. ................... 250/556 |
| 4,095,905 A | * | 6/1978 | Kuni et al. ................. 356/430 |
| 4,171,161 A | * | 10/1979 | Jung ........................... 356/383 |
| 4,196,811 A | * | 4/1980 | Pilesi et al. ................. 209/588 |
| 4,402,604 A | * | 9/1983 | Nash ........................... 356/237 |
| 4,572,666 A | * | 2/1986 | Satake ......................... 356/239 |
| 5,201,576 A | | 4/1993 | Squyres |
| 5,487,472 A | * | 1/1996 | Satake et al. ............... 209/581 |
| 5,845,784 A | * | 12/1998 | Gray et al. ................. 209/577 |

FOREIGN PATENT DOCUMENTS

| | | |
|---|---|---|
| DE | 4127903 | 4/1993 |
| EP | 0443769 | 8/1991 |
| EP | 0705650 | 4/1996 |

* cited by examiner

Primary Examiner—Donald P. Walsh
Assistant Examiner—Daniel K Schlak
(74) Attorney, Agent, or Firm—Lacasse & Associates; Randy W. Lacasse

(57) ABSTRACT

A device and method for sorting of pellets so that pellets containing defects are detected and sorted out. The device includes a light detector arranged over a transparent pellet transport track. A light source is arranged on the opposite side of the track. The detector provides a measurement of a received light intensity, and if the measured intensity is lower than a predetermined threshold value, it can be assumed that a defect is present. The pellet containing the defect is then sorted out by actuating a sorting device. In order to obtain a high precision detection, light is distributed evenly from all directions, including ambient light. The light source fine tunes the balance of the light source and incoming light from other directions. A highly reflective chamber and/or tilted optical axis further provide the desired even distribution of light.

19 Claims, 3 Drawing Sheets

ARRANGEMENT AND METHOD FOR SORTING GRANULES

TECHNICAL FIELD

The present invention relates to a device, a method and a lighting system for detection of defects in and/or on pellets and for sorting of pellets, preferably made of plastics, which differ from a predetermined external appearance.

BACKGROUND OF THE INVENTION

It is previously well known how pellets can be sorted on the basis of a predetermined external appearance. The term pellets refers to ball-shaped or granular objects. Occasionally, pellets may also be called granules. The pellets are preferably made of plastics, but may also be constituted by other materials, such as glass, grains, potatoes, nuts etc. The difficulty as regards the sorting of pellets is, among other things, the actual detection of a defect which may occur in or on a pellet due to the shape or the external appearance (e.g. a certain colour) of the pellet. One reason for why it may be difficult to detect a defect in or on a pellet is that the detection should be evenly carried out over the entire pellet (inside as well as outside), in order to obtain a great accuracy in the detection and to avoid disturbances such as "shadows" and/or reflections (i.e. sections which may be construed as a defect but actually are is just a shadow and/or a reflection). This type of measurement is often very costly and complex. The defects which may occur are, for example, air bubbles, impurities, a differing symmetry, a differing colour etc.

One method of sorting pellets is to first feed the pellets on a conveying belt through feeding means and to convey the pellets on a conveying belt. The feeding means can be constituted by a container for pellets and a mouthpiece in connection with the container which provides a feeding of the pellets. The conveying belt may, for example, be constituted by an endless driving belt. Thereafter, defect pellets which are conveyed on the conveying belt can be detected by means of separation means, i.e. some sort of a detection device. Defect pellets are sorted out by means of sorting means, wherein the sorting means for example can be constituted by a release device for pellets which cooperates with the separation means.

One example of how defects in objects can be detected is described in the U.S. Pat. No. 5,201,576, wherein the detection, is carried out in a spherical chamber which is covered with a highly reflective colour in order to obtain a system which is free from shadows. Furthermore, the chamber is provided with a circularly tubular lamp, two video cameras and a transparent, cylindrical tube having two open ends. The objects are conveyed through the tube, illuminated by the lamp and examined by the cameras. One problem which may occur in connection with this solution is that it may be difficult to adjust the cameras without affecting the light distribution inside the chamber. This is due to the fact that the intensity from the lamp, which is described in the U.S, Pat. No. 5,201,576, will vary inside the chamber, which is due to the fact that the intensity is higher close to the lamp than at a certain distance from the lamp. Another problem may be that the tube affects the light refraction in the form of reflections, i.e. that a mirror image of the lens may appear. Also, this resolution is very complex and costly, while it at the same time only can detect one object at the time.

Another example of how pellets can be sorted is described in EP-A2-0 705 650, wherein the pellets detection is carried out with regard to the colour of the pellets. It seems, however, that the detection only can determine whether the pellet has a differing colour and that the detection thus is unable to determine whether a defect is present inside or outside the pellet, in the form of, for example, air bubbles, impurities, a differing symmetry etc. Also, the detection in EP-A2-0 705 650 seems to have a less even light distribution, which may give rise to disturbances in the detection, such as shadows and/or reflections.

SUMMARY OF THE INVENTION

A device and method for sorting of pellets so that pellets containing defects are detected and sorted out. The device includes a light detector arranged over a transparent pellet transport track. A light source is arranged on the opposite side of the track. The detector provides a measurement of a received light intensity, and if the measured intensity is lower than a predetermined threshold value, it can be assumed that a defect is present. The pellet containing the defect is then sorted out by actuating a sorting device. In order to obtain a high precision detection, light is distributed evenly from all directions, including ambient light. The light source fine tunes the balance of the light source and incoming light from other directions. A highly reflective chamber and/or tilted optical axis further provide the desired even distribution of light.

Detailed preferred embodiments of the method and the device according to the invention will be apparent from the appended dependent claims.

BRIEF DESCRIPTION OF THE DRAWINGS

The invention will be further described in the following with a preferred embodiment and with reference to the annexed drawings, in which.

PREFERRED EMBODIMENTS

Figure 1:
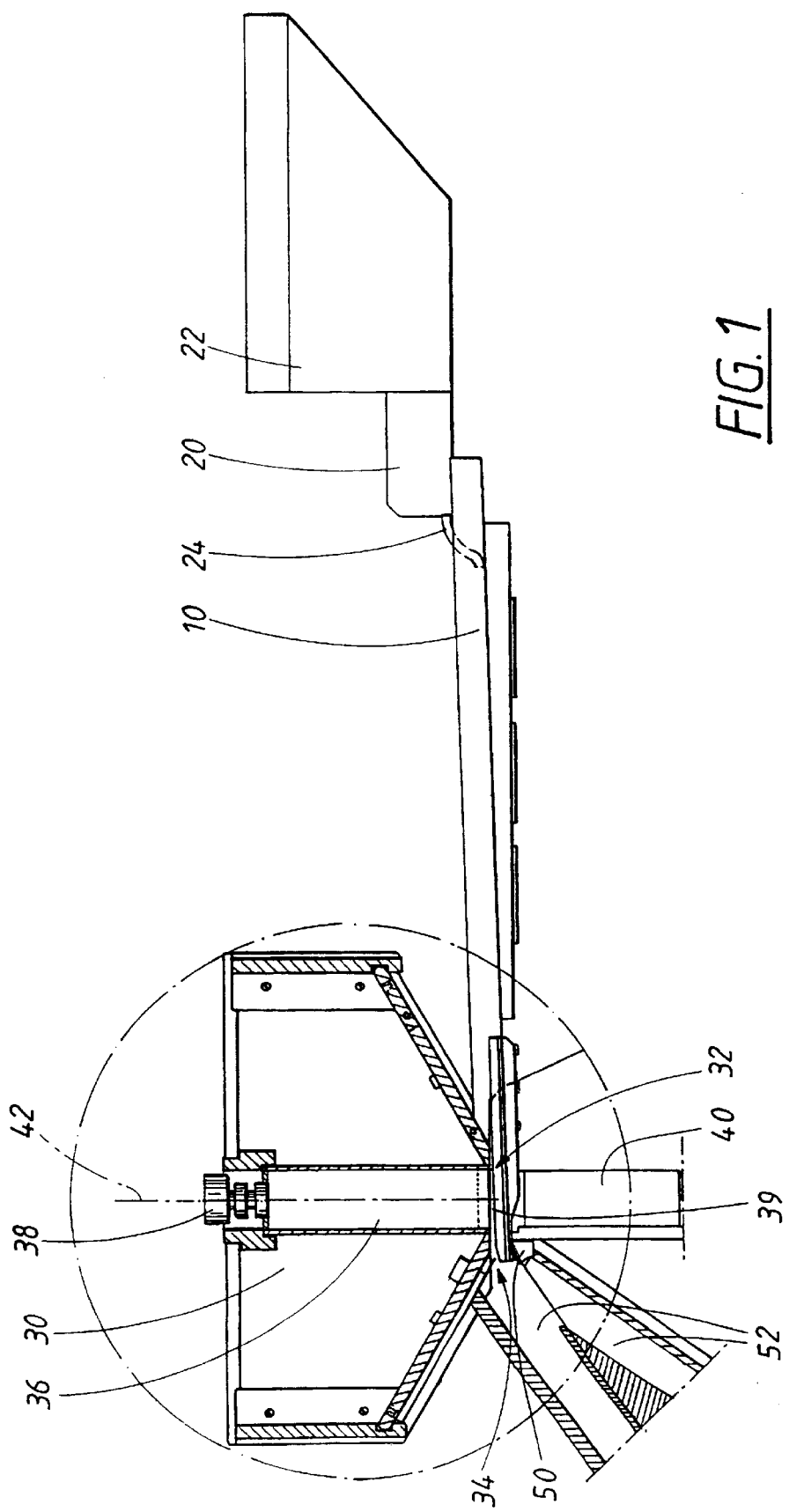
FIG. 1 shows a preferred embodiment of a device for sorting of pellets in accordance with the present invention.

With reference to FIG. 1, a device in accordance with the present invention is shown, said device being intended to sort pellets, which preferably are made of plastics. The device can be provided with a conveying device 10, feeding means 20, separation means 30, and sorting means 50. The main purpose of the conveying device 10 is to convey the pellets, wherein said conveying device for example may be constituted by a conveying belt, an inclined plate, a vibrator and/or the like. The feeding means 20 can, for example, be constituted by a container 22 for pellets and a mouthpiece 24 in connection with said container 22 which provides a feeding of the pellets on the conveying device 10. The pellets are then conveyed further into the separation means 30 in order to detect defects in and/or on the pellets which are conveyed on the conveying device 10. Thus, the separation means 30 is a sort of detection device and will consequently hereinafter be termed thus. When the detection device 30 has detected one or more defect pellets, the sorting means 50 will sort these pellets out. Said sorting means will be described in detail below.

Figure 2:
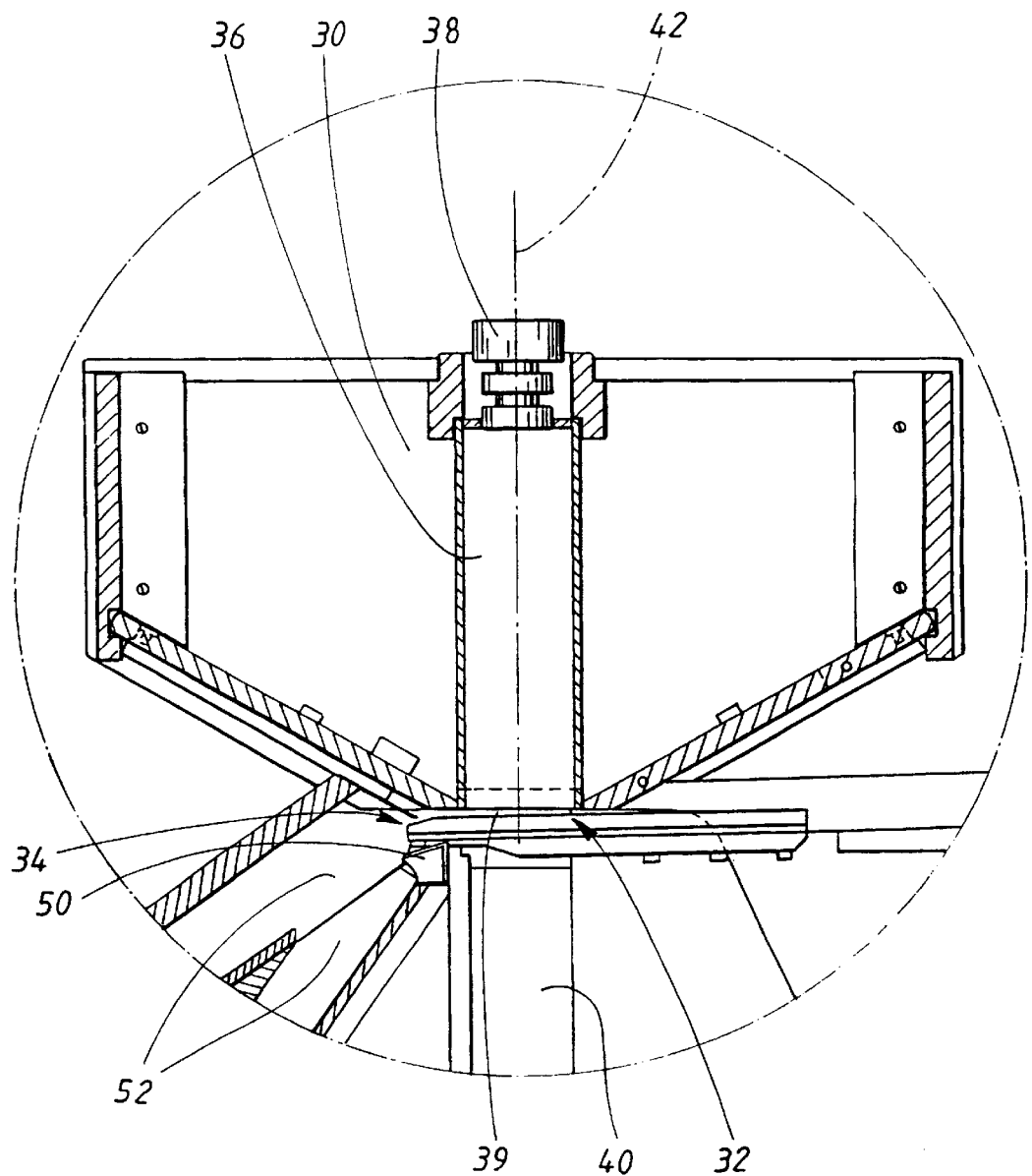
FIG. 2 shows an enlarged view of a detection device which is shown in FIG. 1.

FIG. 2 shows an enlarged view of the detection device which is shown in FIG. 1, said detection device being provided with two recesses which permit pellets to be conveyed through the detection device 30. The recesses 32, 34 function as an inlet 32 and an outlet 34 for pellets.

Furthermore, the detection device is provided with a highly reflective chamber 36 which is arranged between the recesses 32, 34. The chamber 36, which is elongated and has two ends, is provided with a track 39, a detector 38 and a light source 40. The detector 38 and the light source 40 are arranged on either side of the track 39 in order to illuminate and detect pellets which are conveyed on the track 39, wherein the track 39 is arranged in connection with the conveying device 10. The track 39 is light transmittable, i.e. it is transparent or semi-transparent and may, for example, be constituted by a glass plate, by plexiglass or similar material. Said track 39 may form part of the conveying device 10 in the form of a section.

According to the invention, the light source 40 is arranged under the track for directing light towards said track 39, i.e. so that the location of the light source in one end of the chamber makes a concentration of the light in a certain direction possible. The light travels through the track 39 and further into the detector 38 in order to detect defects in and/or on pellets. The detector 38 is arranged in the other end of the chamber and sends a signal to the release device 52, depending upon whether a defect has been detected or not, and releases pellets into the sorting means 50. Thus, this means that one of the ends can be arranged in a plane which is essentially in parallel with the track 39. In this manner, the light will travel with a uniform intensity through the track 39 and further into the detector 38. In the same manner as regards one of the ends, the other end is also arranged in a plane which is essentially in parallel with the track 39. When a defect has been detected, the detector 38 sends a signal to the release device 52 and releases pellets into the sorting means 50.

Preferably, the chamber is evenly illuminated over its entire surface and may for example have circular cross-sections, circular sectors, elliptical cross-sections, spherical cross-sections etc. In order to obtain an even illumination, the interior surface of chamber 36 may, for example, be covered with a reflecting layer 36, such as aluminum or the like. The light source 40 may illuminate the pellets from below, from above and/or all around. A suitable location of the light source 40 may be under, over and/or around the track 39 which is arranged in connection with one end of the chamber.

The chamber 36 may also be provided with an optical axis 42, which can be arranged between the two ends of the chamber. In order to avoid disturbances such as shadows or reflections from, for example, the conveying device 10, it is possible, according to a preferred embodiment, to angularly adjust the detector 38, the light source 40, the two ends of the chamber 36 or the track 39 in relation to the optical axis 42. In all these cases, it may be suitable with an angular adjustment in the range of 0–45°, preferably 2–10°. This means that the ends do not have to lie in a plane which is in parallel with the track, but the ends may also be angularly adjusted in relation to the track within the same angles that are mentioned above. The term shadows, which is mentioned above, refers to sections on the track 39 or on a pellet which may be construed as a defect but in actual fact is just a shadow, which for example may occur due to an uneven illumination over the pellet and/or reflections from the track 39. The term reflection refers, for example, to the light which is reflected towards the track 39, which may be perceived as a mirror image of the detector 38 and/or a reflection from the conveying device 10.

Figure 3A:
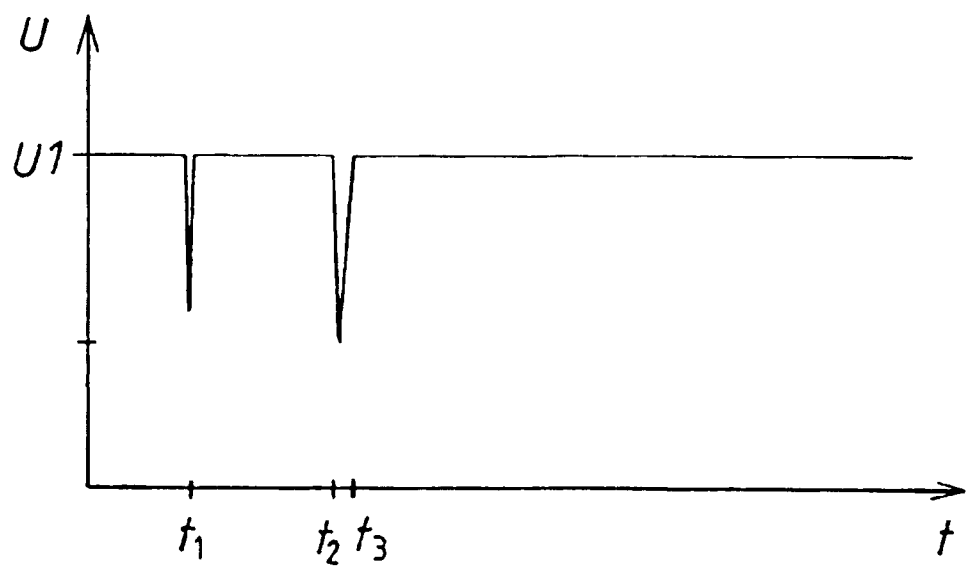
FIG. 3 shows various intensity diagrams.
Figure 3B:
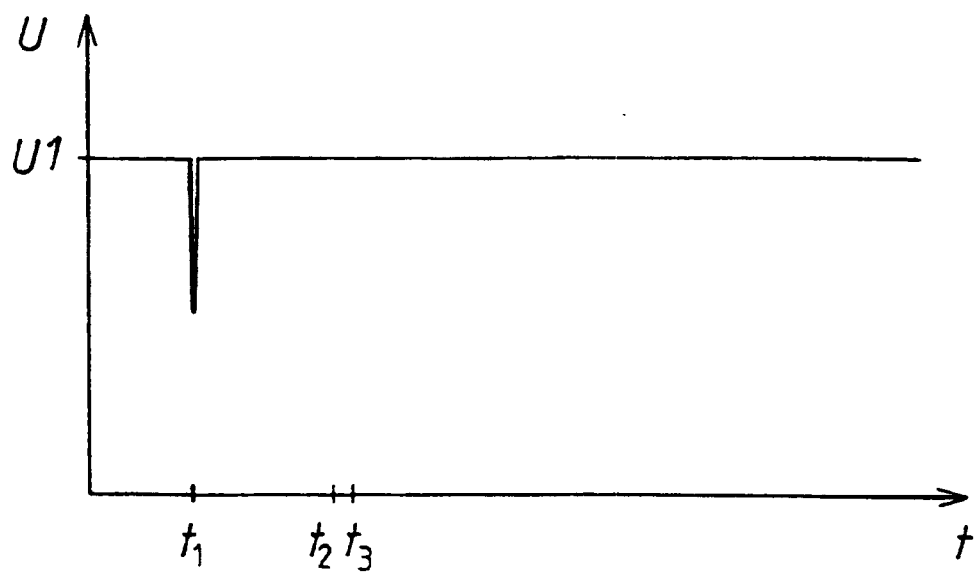

FIG. 3a shows how the detector 38 can perceive its environment without angular adjustment, whereas FIG. 3b shows how the detector 38 perceives the environment with angular adjustment. The intensity U may, for example, be the potential level which the detector obtains during detection. The time t constitutes the time during which the measurement is performed. The level U1 symbolizes a sort of normal state for the measurement, i.e. that no defects has been detected. At the time point t1, a defect occurs which is shown in the form of a potential drop, whereas the potential drop between the time points t2–t3 in FIG. 3a symbolizes a mirror image of the detector 38 and/or a reflection from the conveying device 10 between two pellets. Thus, as is apparent from the diagram in FIG. 3b, an essential advantage is that the detector 38 only detects defects and that no mirror images or reflections are registered between the defects.

The detector 38 may, for example, be provided with focusing means which, for example, comprise a lens system and an optical axis 42, in order to focus the light which passes the track 39, and one or more detector organs (not shown). The detector organs may, for example, be constituted by a CCD-camera or one single detector organ (e.g. a photo-diod), which detects light from a mirror (not shown) which rotates essentially over the pellet, in order to detect defects on the pellet. Furthermore, the detector 38 may be of a scanning type, i.e. the detector may essentially scan the light which passes the track 39, for example by mounting the detector on a movable axle and setting the movable axle in motion either manually or by means of a motor (not shown). The CCD (Charges-Couples Devices) in the camera may in a basic embodiment consist of a tightly packed die of light sensitive MOS-transistors, provided with electrodes, on a semi-conductor substrate of silicon. The detector 38 can detect an occurring defect and the light which passes through the strip. Of course, other detectors 38 than CCD-cameras may be used; for example, photo-diodes, a photo multiplier and other types of photocells may be used.

The primary object of the sorting means 50 is to sort out defect pellets which are detected by means of the detection device 30. The sorting means 50 may, for example, be constituted by a release device 52 for pellets which is cooperating with the detection device 30. This cooperation may, for example, be in the form of a guiding device (not shown) which is connected to the detector 38 and provides the release device 52 with information regarding the external appearance of the pellets. The release device 52 may, for example, be constituted by two or more passages, in which the pellets are intended to be situated. Next to the passages, one or more mouthpieces, e.g. nozzles, is/are situated in order to situate the pellets in the correct passage by means of, for example, air or vacuum. Preferably, the mouthpieces next to the passages are several, which provides a simple method of handling several pellets in parallel, which is due to the fact that the air/vacuum can be directed on the pellets with great precision. Even if the size of the pellets may vary to a great extent, it is desirable that a pellet corresponds fairly well with a mouthpiece. A common size of a pellet may be approximately 2–4 mm, preferably 3 mm. In order for the release device 52 to be able to cooperate and release the pellets into the correct passage, the detector 38 can be connected to a control device (not shown), which provides the release device 52 with information regarding the pellets.

The actual method for sorting pellets, which preferably are made of plastics, may, for example, be carried out by means of the pellets being fed on the conveying device 10 through feeding means 20, wherein the conveying device 10 conveys the pellets up to a detection device 30. The feeding means 20 may, for example, be constituted by a container 22 for pellets, which container preferably is funnel-shaped, and a mouthpiece 24 in connection with the container 22 which provides the feeding of the pellets. When the pellets reach the detection device 30, the pellets are conveyed in through a recess 32 which is provided on the device 30, which recess also may be termed as an inlet 32. When the pellets have passed the inlet 32, defect pellets, which have been conveyed on the conveying device 10, can be detected by means of the pellets being illuminated by means of a light source 40, which is included in the detection device 30. The detection device 30 is constituted by a reflective chamber 36, which is elongated and is provided with two ends. One of the ends is situated in connection with a detector 38 which detects defects in and/or on the pellets. The other end is situated in connection with a track 39, where the pellets are conveyed. The pellets which have entered the detection device 30 are subsequently conveyed out through a recess 34 in the detection device 30, which recess also may be termed as an outlet 34. Thereafter, defect pellets which are detected by means of said separation means 30, are sorted out by means of the sorting means 50. The sorting means 50 may, for example, be constituted by a release device 52 for pellets which cooperates with the detection device 30, wherein the release device 52 for example consists of two or more passages for the pellets. Next to the passages, one or more mouthpieces is/are situated which places/place the pellets in the correct passage by means of, for example, air or vacuum. In order for the release device 52 to be able to cooperate and release the pellets into the correct passage, the detector 38 can be connected to a control device (not shown), which provides the release device 52 with information regarding the pellets.

Although the disclosed embodiments of the present invention have been described in detail with reference to the appended drawings, it should be realized that the invention is not limited to these particular embodiments and that various variations or modifications can be accomplished within the scope of the appended claims by a person skilled in the art. For example, the release device 52 can place the pellets into the correct passage by means of one or more connecting rods, instead of by means of air or vacuum.

What claimed is:

1. A device for sorting of pellets, said device comprising:
   a conveying device for conveying pellets;
   feeding means for feeding pellets on said conveying device;
   detection device for detecting defective pellets which are conveyed on said conveying device;
   sorting means for sorting out said defective pellets which are detected by means of said detection device, and
   said sorting means comprises a release device for pellets which cooperates with said detection device, and said detection device comprises two recesses, which permit pellets to be conveyed through the detection device, wherein a chamber is arranged between said recesses, and wherein the chamber is operative with a light transmittable section of said track, a detector and a light source, wherein the detector and the light source are arranged on either side of the section in order to illuminate and detect pellets which are conveyed on the section, wherein the chamber is elongated and has two ends, that the light source is directed into one end of the chamber in the direction towards said light transmittable section so that the light travels through the light transmittable section and further into the detector in order to detect said defective pellets, wherein the detector is arranged in a distal end of the chamber and sends a signal to the release device depending upon whether a defect has been detected or not and releases pellets into the sorting means.

2. The device according to claim 1, wherein said chamber is provided with an optical axis, which is arranged between the two ends of the chamber.

3. The device according to claim 2, wherein one or more of said: light source, two ends of the chamber, light transmittable section, or track is set at an angle with respect to said optical axis.

4. The device according to claim 3, wherein said angle is in a range which exceeds 0, but which is below 45°.

5. The device according to claim 3, wherein said angle is in a range which exceeds 2°, but which is below 10°.

6. The device according to claim 1, wherein said device is provided with one or more mouthpieces, preferably nozzles.

7. The device according to claim 1, wherein said detector is connected to a guiding device which provides the release device with information regarding the pellets.

8. The device according to claim 1, wherein said pellets are plastic.

9. The device according to claim 1, wherein said chamber is reflective.

10. A method for sorting of pellets, for which method a detection device is used and wherein said device comprises two recesses which permit pellets to be conveyed through the detection device, a reflective chamber which is situated between said recesses, wherein the reflective chamber is operative with a light transmittable section, a detector and a light source, said method comprising:
    conveying pellets on a conveying device, wherein said light transmittable section forms part of said conveying device;
    feeding pellets on said conveying device through feeding means;
    illuminating pellets by means of the light source, which is operative with the detection device;
    detecting defective pellets by means of said detection device, wherein pellets are conveyed on said conveying device in through one of said recesses, and
    sorting out said defective pellets by means of said sorting means, said defective pellets being detected by means of said detection device, wherein
    said sorting means comprises a release device for pellets which cooperates with said detection device, and wherein the detector and the light source are arranged on either side of the light transmittable section which illuminates and detects pellets which are conveyed on the section, the chamber which is elongated and is provided with two ends has the light source directed into one end of the chamber, wherein the light travels in the direction towards said light transmittable section, further through the light transmittable section and into the detector, wherein the detector, which is situated in a distal end of the chamber, detects defective pellets and sends a signal to the release device depending upon whether a defect has been detected or not and releases pellets into the sorting means.

11. The method according to claim 10, wherein said chamber is provided with an optical axis which is situated between the two ends of the chamber.

12. The method according to claim 11 wherein one or more of said: light source, two ends of the chamber, light transmittable section, or track is set at an angle with respect to said optical axis.

13. The method according to claim 12 wherein said angle is in a range which exceeds 0°, but which is below 45°.

14. The method according to claim 12 wherein said angle is in a range which exceeds 2°, but which is below 10°.

15. The method according to claim 12, wherein said pellets are plastic.

16. A detection device for detection of defective pellets, said detection device comprising:

two recesses which permit pellets to be conveyed through the detection device, and a reflective chamber which is arranged between said recesses, wherein said reflective chamber is operative with a light transmittable section, a detector and a light source, wherein the detector and the light source are arranged on each side of the track in order to illuminate and detect pellets which are conveyed on the track, the chamber is elongated and has two ends, that the light source is directed into one end of the chamber in the direction towards said track, so that the light travels through the section and further into the detector in order to provide a detection of said defective pellets, and that the detector is arranged in a distal end of the chamber.

17. The device according to claim 16, wherein said chamber is provided with an optical axis, which is arranged between the two ends of the chamber.

18. The device according to claim 17, wherein one or more of said: light source, two ends of the chamber, light transmittable section, or track is set at an angle with respect to said optical axis.

19. The device according to claim 18, wherein said angle is in a range which exceeds 0°, but which is below 45°.

* * * * *